United States Patent
Murphy

(10) Patent No.: US 8,753,331 B2
(45) Date of Patent: Jun. 17, 2014

(54) ADJUSTABLE VALVE SETTING WITH MOTOR CONTROL

(75) Inventor: John Murdock Murphy, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 13/585,227

(22) Filed: Aug. 14, 2012

(65) Prior Publication Data
US 2012/0310139 A1 Dec. 6, 2012

Related U.S. Application Data

(63) Continuation of application No. 12/614,580, filed on Nov. 9, 2009, now Pat. No. 8,241,240.

(51) Int. Cl.
*A61B 5/03* (2006.01)

(52) U.S. Cl.
USPC ............. 604/891.1; 604/9; 137/524; 128/903

(58) Field of Classification Search
CPC ... A61B 5/0031; A61B 5/031; F16K 37/0041
USPC ............. 604/9, 891.1; 137/524, 530; 128/903
See application file for complete search history.

(56) References Cited

U.S. PATENT DOCUMENTS

| | | | |
|---|---|---|---|
| 4,026,276 A | 5/1977 | Chubbuck | |
| 4,156,422 A | 5/1979 | Hildebrandt et al. | |
| 4,360,007 A | 11/1982 | Levy et al. | |
| 4,540,400 A | 9/1985 | Hooven | |
| 4,551,128 A | 11/1985 | Hakim et al. | |
| 4,595,390 A | 6/1986 | Hakim et al. | |
| 4,608,992 A | 9/1986 | Hakim et al. | |
| 4,615,691 A | 10/1986 | Hakim et al. | |
| 4,676,772 A | 6/1987 | Hooven | |
| 4,772,257 A | 9/1988 | Hakim et al. | |
| 5,425,382 A | 6/1995 | Golden et al. | |
| 5,637,083 A | 6/1997 | Bertrand et al. | |
| 5,643,194 A | 7/1997 | Negre | |
| 5,643,195 A | 7/1997 | Drevet et al. | |
| 5,879,297 A | 3/1999 | Haynor et al. | |
| 5,928,182 A | 7/1999 | Kraus et al. | |
| 6,050,969 A | 4/2000 | Kraus | |
| 6,129,668 A | 10/2000 | Haynor et al. | |
| 6,206,835 B1 * | 3/2001 | Spillman et al. | 600/485 |
| 6,216,028 B1 | 4/2001 | Haynor et al. | |
| 6,264,635 B1 * | 7/2001 | Wampler et al. | 604/151 |
| 6,326,760 B1 | 12/2001 | Cardoletti et al. | |
| 6,391,019 B1 | 5/2002 | Ito | |
| 6,439,538 B1 | 8/2002 | Ito | |

(Continued)

FOREIGN PATENT DOCUMENTS

EP 0735662 A2 10/1996

*Primary Examiner* — Eric Keasel
(74) *Attorney, Agent, or Firm* — Dicke, Billig & Czaja, PLLC

(57) ABSTRACT

An implantable medical device is disclosed that includes a valve body and a valve rotor adjustable with respect to the valve body. A tool can be utilized to determine and control a position of the valve rotor with respect to the valve body. The tool can include a valve body position reader, a valve rotor position reader and a valve rotor position controller to determine a valve setting for the device and adjust the valve setting as desired.

18 Claims, 5 Drawing Sheets

(56) References Cited

U.S. PATENT DOCUMENTS

| | | |
|---|---|---|
| 6,474,360 B1 | 11/2002 | Ito |
| 6,485,449 B2 | 11/2002 | Ito |
| 6,684,904 B2 | 2/2004 | Ito |
| 6,702,249 B2 | 3/2004 | Ito |
| 6,840,917 B2 | 1/2005 | Marion |
| 6,883,241 B2 | 4/2005 | Moskowitz et al. |
| 6,951,059 B2 | 10/2005 | Moskowitz et al. |
| 7,118,549 B2 | 10/2006 | Chan |
| 7,334,582 B2 | 2/2008 | Bertrand et al. |
| 7,334,594 B2 | 2/2008 | Ludin |
| 7,422,566 B2 | 9/2008 | Miethke |
| 7,443,128 B2 | 10/2008 | Bieler et al. |
| 7,485,105 B2 | 2/2009 | Wolf |
| 7,736,312 B2 | 6/2010 | Taylor et al. |
| 7,758,536 B2 | 7/2010 | Cabaud et al. |
| 7,766,855 B2 | 8/2010 | Miethke |
| 7,842,004 B2 | 11/2010 | Kassem |
| 7,856,987 B2 | 12/2010 | Bertrand et al. |
| 7,921,571 B2 | 4/2011 | Moureaux et al. |
| 8,038,641 B2 | 10/2011 | Soares et al. |
| 8,057,422 B2 | 11/2011 | Wolf, II |
| 8,123,714 B2 | 2/2012 | Ludin et al. |
| 8,241,240 B2 | 8/2012 | Murphy |
| 2002/0022793 A1 | 2/2002 | Bertrand et al. |
| 2006/0186846 A1 | 8/2006 | Lassen |
| 2008/0221436 A1 | 9/2008 | Bertrand et al. |

\* cited by examiner

ADJUSTABLE VALVE SETTING WITH MOTOR CONTROL

CROSS-REFERENCE TO RELATED APPLICATIONS

This application is a continuation of U.S. application Ser. No. 12/614,580, filed on Nov. 9, 2009, and entitled "Adjustable Valve Setting with Motor Control," now U.S. Pat. No. 8,241,240, the contents of which are incorporated herein by reference.

BACKGROUND

1. Technical Field

This disclosure relates generally to surgically implanted physiological shunt systems and related flow control devices. More particularly, the present disclosure relates to a position indicator and adjustment tool for such shunt systems having variable pressure settings for the one-way flow control valves controlling the flow of Cerebral Spinal Fluid (CSF) out of a brain ventricle and preventing backflow of fluid into the brain ventricle.

2. Description of Related Art

A typical adult has a total of about 120-150 cubic centimeters (cc) of CSF with about 40 cc in ventricles in the brain. A typical adult also produces about 400-500 cc/day of CSF, all of which is reabsorbed into the blood stream on a continuous basis.

Sometimes, the brain produces excess CSF or there can be a blockage of the normal CSF pathways and or absorption sites resulting in a condition know as hydrocephalus. Hydrocephalus is a condition of excessive accumulation of CSF in the ventricles or brain tissue. Hydrocephalus can result from genetic conditions, from trauma to the brain or as a person ages.

Excessive accumulation of CSF, due to hydrocephalus or other causes, manifests itself as increased pressure within the brain. Whatever the cause, over time, this increased CSF pressure causes damage to the brain tissue. It has been found that relieving the CSF pressure is therapeutically beneficial. This relief is usually performed by draining CSF from the ventricles.

Patients with hydrocephalus normally require, at least over some time period, continuous drainage of excess CSF to maintain normal CSF pressure in the brain. Excessive CSF accumulated in the ventricles of the brain is typically drained away from the brain using a shunt system.

Where hydrocephalus is a chronic condition, the shunt system typically drains the CSF into the patient's peritoneal cavity or into the patient's vascular system. Such shunt systems typically have a catheter implanted in the ventricle of the brain. The catheter is connected to a fluid control device which is in turn connected to a catheter which empties in to the patient's peritoneal cavity or into the patient's vascular system. An example of a fluid control device is shown in U.S. Pat. No. 5,637,083 issued to William J. Bertrand and David A. Watson on Jun. 10, 1997 entitled "Implantable Adjustable Fluid Flow Control Valve", the teaching of which is incorporated herein in its entirety by reference. Current fluid control devices include an inlet connector, an outlet connector and a valve positioned between the inlet connector and the outlet connector. The valve includes a mechanism to control fluid flow through the valve. In some instances, the mechanism includes a magnet embedded within the valve. Rotating a rotor or otherwise shifting of the rotor position changes the internal configuration of the mechanism. Changing the internal configuration of the mechanism produces a variety of pressure or flow characteristics for the valve. As the internal configuration of the valve changes, the pressure or flow characteristics of the valve change.

In use, the valve is subcutaneously placed on the patient's skull. The catheter going to the patient's ventricle is attached to the inlet connector. The catheter going to the patient's peritoneal cavity or vascular system is attached to the outlet connector. In this way, a direction of flow is established from the inlet connector through the valve to the outlet connector. Changing the internal configuration of the mechanism by coupling the external magnet to the internal magnet and rotating the external magnet effects a movement internal to the shunt and produces a variety of pressure or flow characteristics through the valve.

It is desirable to have a number of different settings in order to achieve different pressure and/or flow characteristics of the valve. A problem with current adjustable valves is that once implanted, it is difficult to determine the setting of the valve and/or adjust the setting of the valve. Having more settings for the valve only makes determining and/or adjusting the valve setting more difficult. With some adjustable valves, x-ray images are used to determine the current state or post adjustment state of the valve. By requiring an x-ray, it is time consuming and costly to determine and adjust the valve setting, as well as not being in the best interest of the patient due to X-ray exposure issues.

SUMMARY

Concepts presented herein relate to determining and/or adjusting a setting for an implantable medical device. In one embodiment, the device includes a valve body and a valve rotor adjustable with respect to the valve body. A tool can be utilized to determine and control a position of the valve rotor with respect to the valve body.

The tool includes a valve body position reader, a valve rotor position reader and a valve rotor position controller. The valve rotor position controller includes a stator having a plurality of stator coils and a driver. The valve body position reader determines an orientation of the valve body and the valve rotor position reader is configured to determine a position of the valve rotor with respect to the valve body. The driver is electrically coupled to the stator to provide current to the stator coil to alter the position of the valve rotor.

In another aspect, a system includes an implantable medical device having a valve body and a valve rotor adjustable with respect to the valve body. The valve rotor includes a permanent magnet. The system also includes a positioning tool having a valve body position reader, a valve rotor position reader and a valve rotor position controller. The valve rotor position controller includes a stator with a plurality of stator coils and a driver. The valve body position reader and the valve rotor position reader determine an orientation of the valve body and a position of the valve rotor with respect to the valve body. The driver is electrically coupled to the stator to provide current to the stator coils in order to selectively position the valve rotor with respect to the valve body.

In another aspect, a method includes providing a positioning tool having an excitation coil, a sensing coil, at least one magnetic sensor and a stator with a plurality of stator coils. The positioning tool is placed proximate to an implantable medical device. The implantable medical device includes a valve body and a valve rotor. The valve body includes a resonant circuit and the valve rotor includes a permanent magnet. The resonant circuit is energized using the excitation coil and return energy is sensed with the sensing coil. An orientation of the valve body with respect to the tool determined based on the sensed energy. A position of the valve rotor with respect to the positioning tool is determined using the at least one magnet sensor. A position of the valve rotor with respect to the valve body is then determined based on the orientation of the valve body with respect to the tool and the position of the valve rotor with respect to the tool.

DETAILED DESCRIPTION

Figure 1:
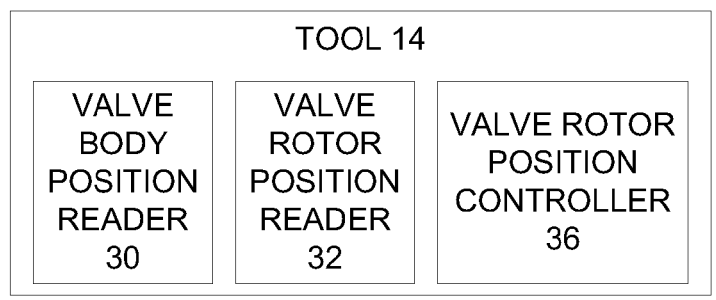
FIG. 1 is a schematic block diagram of an adjustable shunt system.
Figure 1:
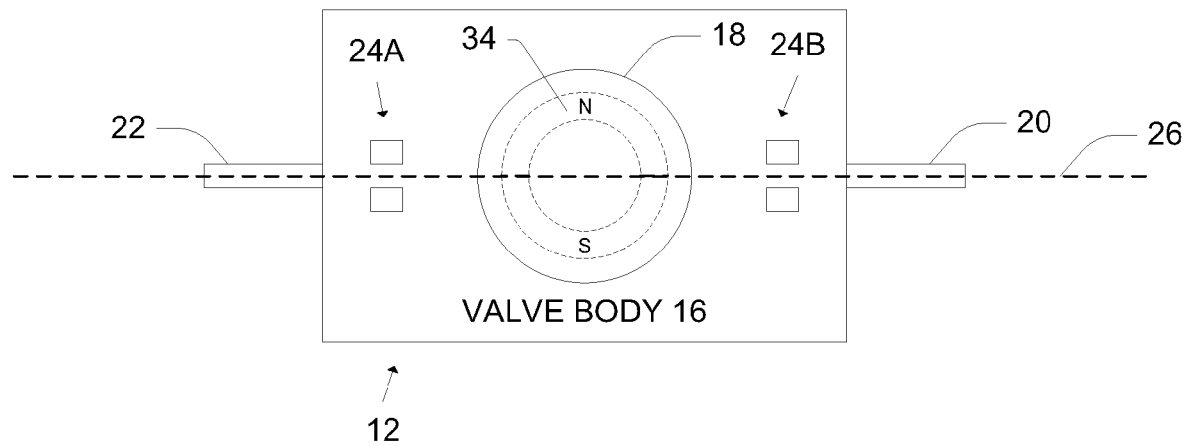

FIG. 1 is a schematic block diagram of an adjustable shunt system 10 including an implantable flow control device 12 (e.g., a shunt) and an electronic valve reader and adjustment tool 14. The device 12 includes a valve body 16 and a valve rotor 18 that is adjustable with respect to the valve body 16. Fluid is allowed to flow through the valve body 16 from an inlet connector 20 to an outlet connector 22 depending on a position of valve rotor 18 with respect to valve body 16. The valve rotor 18 defines a number of unique settings to alter pressure and/or flow characteristics of fluid through device 12. Valve rotor 18 can be of different configurations, for example being rotatable with respect to valve body 18 or being adjustable linearly with respect to valve body 18.

Tool 14 includes a valve body position reader 30 that is configured to determine a position (i.e., orientation) of valve body 16 with respect to the tool 14. In one embodiment, valve body 16 includes at least one resonant circuit. In the embodiment illustrated in FIG. 1, two pairs of resonant circuits (or coils) 24A and 24B are coupled to the valve body with a fixed orientation. In one example, each resonant circuit can be formed of a capacitor and an inductor. Pair 24A includes two circuits spaced apart from a longitudinal axis 26 of the valve body 16 while pair 24B is positioned on an opposite side of valve rotor 18 from pair 24A and includes two circuits on either side of longitudinal axis 26. As discussed below, the valve body position reader 30 can include one or more coils to excite (i.e., energize) and sense return energy from the pairs of circuits 24A, 24B. To this end, valve body position reader senses energy 30 from circuit pairs 24A, 24B to determine the orientation of valve body 16 with respect to tool 14. In one example, valve body position reader 30 can compare differences in return energy from pair 24A and 24B to determine the orientation of valve body.

Once the position of valve body 16 with respect to tool 14 is determined, a position of the valve rotor 18 with respect to the tool 14 can be determined using a valve rotor position reader 32. In one embodiment, valve rotor 18 includes an embedded permanent magnet 34 that forms a rotor of a brushless motor. In one embodiment, the motor can further be sensorless.

Valve rotor position reader 32 can include a plurality of magnetic sensors (e.g., magnetometers) to sense the position of permanent magnet 34 and thus valve rotor 18. Given the position of the valve body 16 determined by valve body position reader 30 and the position of rotor 18 as determined by the valve rotor position reader 32, a valve setting for device 12 can be determined. In one embodiment, tool 14 includes a suitable memory device for determining the valve setting based on the determined orientation of valve body 16 and position of valve rotor 18.

To drive valve rotor 18 to a different position and thus change the valve setting of device 12, a valve rotor position controller 36 forms a stator and includes coils to position valve rotor 18 with respect to valve body 16. These coils may or may not be the same as those used to determine the orientation of valve body 16. In this respect, the position of valve rotor 18 can be adjusted continuously, in one embodiment, so that a large number of settings can be provided, each setting providing a unique pressure setting. In one embodiment, adjustments of the valve rotor 18 can be 1° or less. In other embodiments, the adjustments can be approximately 2°, approximately 5°, approximately 10° and/or combinations thereof. In any extent, the number of different adjustments can correspond to a large number of unique settings for device 12, for example five settings, 10 settings, 20 settings or more, each setting providing different pressure and/or flow characteristics for device 12.

Figure 2:
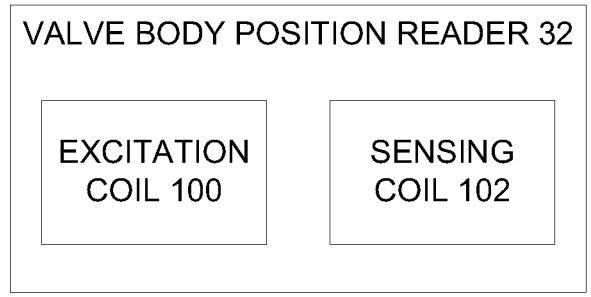
FIG. 2 is a schematic block diagram of components in a valve body position reader.

FIG. 2 is a block diagram illustrating an embodiment of valve body position reader 30 within electronic valve reader and adjustment tool 14. In the embodiment illustrated, valve body position reader includes an excitation coil 100 and a sensing coil 102. In an alternative embodiment, coils 100 and 102 can be the same coil. In still a further embodiment, more coils can be used to excite circuit pairs 24A and 24B. Excitation coil 100 is tuned to excite circuit pairs 24A and 24B. After excitation, sensing coil 102 is used to sense energy returned by the circuit pairs 24A and 24B so as to determine the orientation of the pairs 24A, 24B and thus an orientation of valve body 16 with respect to tool 14.

Figure 3:
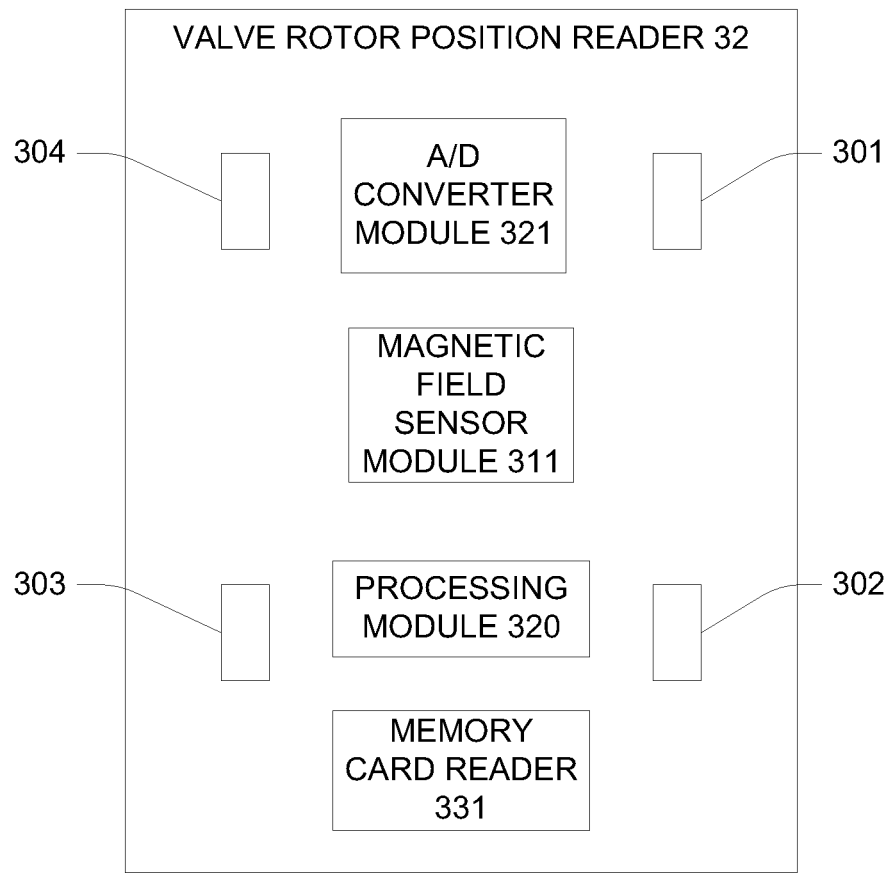
FIG. 3 is a schematic block diagram of components for a valve rotor position reader.

FIG. 3 is a block diagram illustrating valve rotor position reader 32 within electronic valve reader and adjustment tool 14. The valve rotor position reader 32 is constructed using a plurality of magnetic field sensor modules 301-304. In one embodiment, the magnetic field sensor modules 301-304 are magnetometers. Each of these four sets of magnetic field sensor modules 301-304 contain three separate sensors so as to measure the full, three-dimensional vector magnetic field detected by the particular module at its location. The reader 30 also contains an analog-to-digital converter module 321 and a combined magnetic field sensor module 311 to electronically process the signals generated by the magnetic field sensor modules 301-304 to obtain digital measurements corresponding to the observed magnetic field. The reader 32 may also contain an extra magnetic field sensor outside of the range of the rotor magnet used to measure the ambient field strength of the earth. This value may be used later to correct measurements provided by the other sensors.

These digital measurements of the observed magnetic field are subsequently processed within a processing module 320 to determine the location and orientation of the permanent magnet 34 within a field of view for the reader 32. The processing module performs operations upon the measured magnetic field data to determine the magnetic field generated by the magnet 34 while subtracting an estimate for ambient and environmental magnetic field also observed by the magnetic field sensor modules 301-304. The processing performed in determination of the location and orientation of the magnetic indication device can be performed in different ways. U.S. Pat. Nos. 5,879,297; 6,129,668 and 7,334,582 all describe approaches to determining locations and orientations of medical devices; the contents of which are hereby incorporated by reference in their entirety. Processing module 320 can also communicate with valve body position reader 30 to determine the valve setting of device 12 based on the position of valve body 16 determined by reader 30 and the position of valve rotor 18 determined by reader 32, as discussed below.

The reader 32 may further contain a memory card reader 231 for accepting computer readable storage media. In one embodiment, this storage media may include compact flash, start media, secure digital, and memory stick memory cards for providing the reader 32 (and thus tool 14) replaceable memory containing data usable by the reader 32. For example, the implantable flow control device 12 may permit fluid to flow at a particular pressure setting that corresponds to a particular setting on the valve. When the reader 32 determines the valve setting, the data from the memory card may be used to display the corresponding pressure setting. Because the valve-to-pressure setting may vary from particular models of implantable flow control devices, the use of a memory card corresponding to the model of the flow control device will permit the reader device to easily display pressure values for a wide variety of flow control devices without needing to maintain all of the valve to pressure setting data for all devices at one time.

Figure 4:
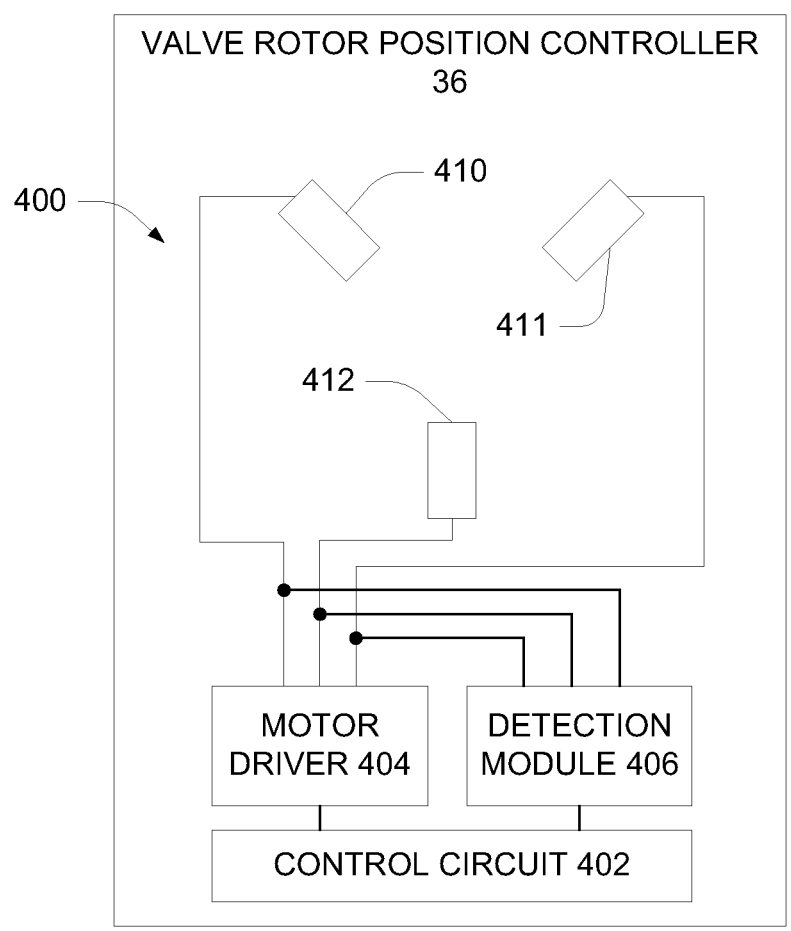
FIG. 4 is a schematic block diagram of components of a valve rotor position controller.

FIG. 4 is a schematic block diagram of valve rotor position controller 36. The controller 36 includes a stator 400, a control circuit 402 and a motor driver 404. If desired, valve rotor position controller 32 can also include a detection module 406. Motor driver 404 is coupled to a plurality of stator coils 410-412 for positioning of valve rotor 18. Any number of stator coils can be used, such as in a range of one to ten stator coils. In a further embodiment, six stator coils are used. In particular, control circuit 302 provides current to the driver 304 in order to apply magnetic forces to permanent magnet 34. These magnetic forces cause magnet 34 to rotate, thus altering a valve setting of device 12. Valve rotor position reader 32 can continuously monitor the position of magnet 34 so as to adjust device 12 to the desired valve setting.

In an alternative embodiment, detection module 406 detects voltages in stator coils 410-412, which can be used to determine a position of valve rotor 18. Position determination and control of a motor is further described in U.S. Pat. Nos. 6,326,760 and 7,443,128, the contents of which are both hereby incorporated by reference in their entirety.

In one embodiment, drive currents to the stator 400 are selectively applied and removed by motor driver 404 as directed by control circuit 402. Using detector module 406, a resulting electromotive force (EMF) voltage is sensed in each of the stator coils 410-412 after the drive currents are removed. From these EMF voltages, the position of the valve rotor 18 can be determined with respect to the tool 14. Once the valve rotor position is determined with respect to the tool 14, calculations can be made to determine the position of the valve rotor 18 with respect to the valve body 16.

For example, as illustrated, each of the stator coils 410-412 represent a motor phase for driving valve rotor 18 with respect to valve body 16. The three phases are illustratively separated by 120° and can be positioned to be equally spaced around the valve rotor 18. By selectively providing drive currents to the stator coils and switching the drive currents off, EMF voltages are induced in the stator windings by the permanent magnet 34 of valve rotor 18, which is indicative of the position of the valve rotor 18 with respect to tool 14. If the drive currents are provided with a phase shift from one phase to the next phase, this results in a shift between the resultant EMF voltages in respective stator coils 410-412. Detector 406 is used to sense the EMF voltages and provide an indication of the voltage to control circuit 402.

The frequency of the drive current pulses is chosen as a function of both the characteristics of the motor and its current status. After the drive current is turned off, for instance at a time $t_0$, there is a stabilization period $\delta t$, after which the induced voltage in each motor phase is measured, for instance at a time $t_m$. From these measured induced voltages, the valve rotor position can be determined. By way of example, the rotor position in a two-axis system can be determined from the induced voltages measured in a three-phase synchronous motor using the following formulae:

$$U_a = V1;$$

$$U_b = (V2 - V3)/\sqrt{3}$$

where $U_a$ and $U_b$ are two voltages proportional to the two components of the rotor position vector in said two-axis system and V1, V2, and V3 are the measured induced voltages in the three motor phases (i.e., stator coils 410-412), respectively. It should be noted however that two measured induced voltages only are actually required since the third one can be determined using the equation V1+V2+V3=0. Based on the voltages, a measured angular position $\theta$ is for valve rotor 18 is determined by using the formula $\theta = \arctan(U_a/U_b)$. Other methods, well known to those skilled in the art, may also be used, such as derivation of the determined position or calculation of the change in rotor position as a function of time.

Figure 5:
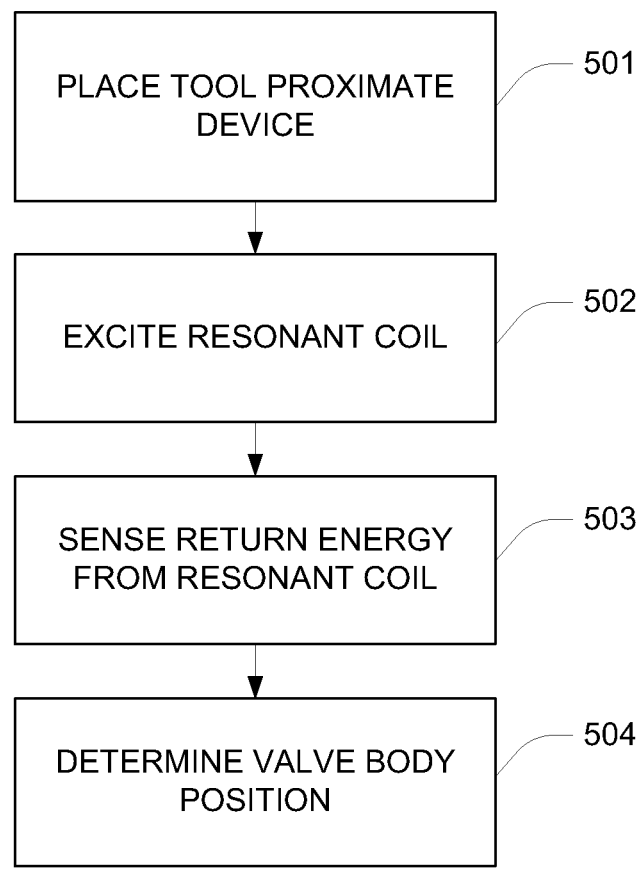
FIG. 5 is a flow diagram of a method for determining an orientation of a valve body with respect to a tool.

FIG. 5 illustrates a flowchart of a method for use of electronic valve reader and adjustment tool 14. The method for determining the position of valve body 16 with respect to tool 14 begins by placing 501 the tool 14 proximate the device 12. Next, the circuit pairs 24A and 24B are excited 502 by excitation coil 100. In particular, excitation coil 100 can be tuned to energize circuit pairs 24A, 24B. Return energy from the circuit pairs 24A and 24B are sensed 503 and a determination 504 of the orientation of valve body 16 with respect to tool 14 is made from the sensed energy.

Figure 6:
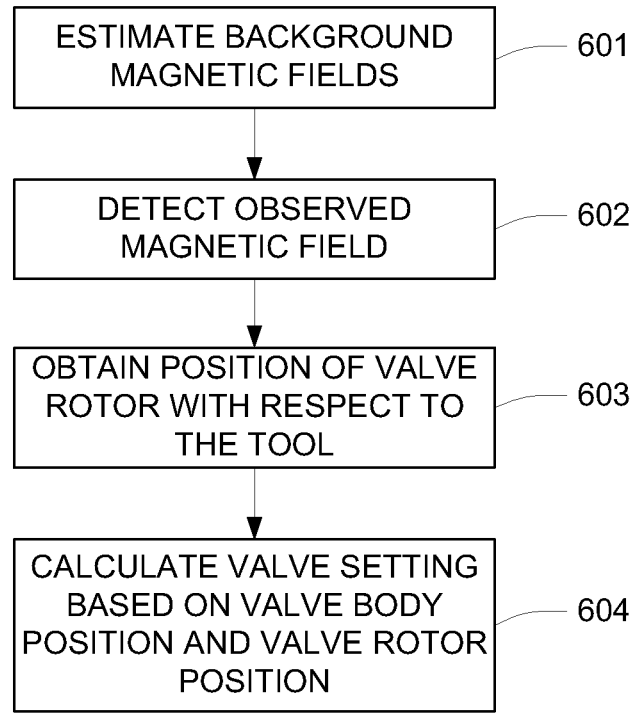
FIG. 6 is a flow diagram of a method for use in calculating a valve setting.

FIG. 6 illustrates a flowchart of a method for calculating a valve setting for device 12 once the tool 14 has determined the position of valve body 16. To determine the valve setting, the position of valve rotor 18 with respect to tool 14 is determined by the reader 32 by estimating background magnetic fields 601. Next, observed magnetic fields 602 are detected from all sources. The background magnetic fields estimate 601 is subtracted from the observed values 602 to obtain a position and orientation for the valve rotor 18 based on magnet 34. The detected magnetic field measurements and processed position and orientation for the valve body 18 are repeated at a rate of several times per second. Given the positions of the valve body 16 and the valve rotor 18, a valve setting is calculated 604 for device 12. The valve setting is indicative of flow characteristics through device 12. Once the setting is determined, the tool 14 can be used to adjust the setting as desired.

Figure 7:
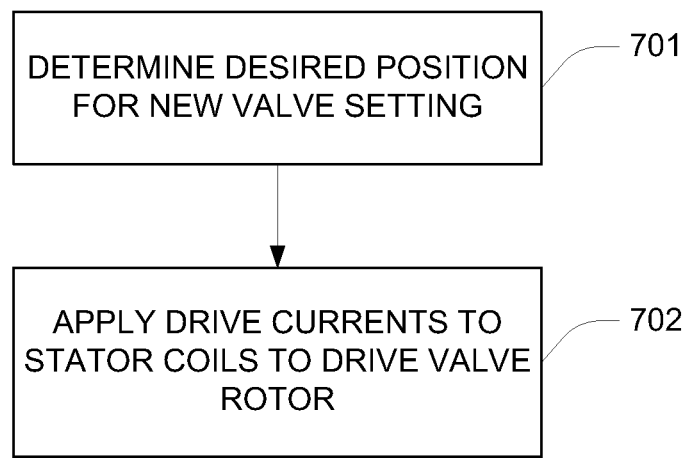
FIG. 7 is a flow diagram of a method for use in adjusting a valve setting.

FIG. 7 illustrates a flowchart of a method for adjusting the position of valve rotor 18 with respect to valve body 16. Based on the valve setting calculated 604, a desired position for a new valve setting can be determined 701, so as to alter the pressure and/or flow characteristics through device 12. In one embodiment, pressure flow characteristics are known such that a position of the valve rotor 18 with respect to the valve body 16 corresponds to a particular setting. Once the desired setting is determined, the motor driver 404 can drive the stator coils 410-412 in order to position the valve rotor 18 with respect to the valve body 702. As a result, then, a large number of unique settings for the implantable flow control device 12 can selectively be determined and/or adjusted using tool 14, even while device 12 is placed subcutaneously.

Although the present disclosure has been described with reference to preferred embodiments, workers skilled in the art will recognize that changes can be made in form and detail without departing from the spirit and scope of the present disclosure.

What is claimed is:

1. A positioning tool for controlling a valve rotor with respect to a valve body in an implantable medical device, the device defining a direction of flow from an inlet to an outlet, comprising:
   a valve body position reader including at least one coil configured to excite a circuit on the valve body and sense energy from the circuit after the circuit is excited to determine an orientation of the direction of flow for the device with respect to the positioning tool;
   a valve rotor position reader including a magnetic sensor to sense a position of the valve rotor with respect to the positioning tool;
   a processor coupled to the valve body position reader and the valve rotor position reader and configured to determine a position of the valve rotor with respect to the valve body based on the orientation of the device and the position of the valve rotor with respect to the positioning tool; and
   a valve rotor position controller adapted to alter the position of the valve rotor with respect to the valve body.

2. The positioning tool of claim 1 wherein the valve rotor position reader is configured to calculate the valve rotor position using magnetic sensors.

3. The positioning tool of claim 1 and further comprising a stator configured to measure valve rotor position based on back EMF in a plurality of stator coils.

4. The positioning tool of claim 1 wherein the valve rotor is rotatable with respect to the valve body.

5. The positioning tool of claim 1 wherein the valve rotor position reader includes a plurality of magnetic sensors for determining the position of the valve rotor.

6. The positioning tool of claim 1 wherein the valve body position reader includes a first coil to energize the circuit in the valve body and a second coil to determine the position of the valve body.

7. The positioning tool of claim 1 wherein the valve body position reader includes a single coil to energize the circuit in the valve body and to determine the position of the valve body.

8. The positioning tool of claim 1 wherein the processor is configured to calculate a valve setting for the implantable medical device from a plurality of valve settings, the valve setting being indicative of pressure and/or flow characteristics of fluid through the device.

9. The positioning tool of claim 1 wherein the valve rotor position controller includes a plurality of stator coils within the tool such that, when the tool is positioned proximate the device, the plurality of stator coils are positioned equally about the valve rotor.

10. The positioning tool of claim 9 wherein the plurality of stator coils include six stator coils that can be positioned equally about the valve rotor.

11. The positioning tool of claim 9 wherein the valve rotor position controller further includes a control circuit and a driver configured to provide drive currents to the plurality of stator coils to induce electromagnetic force voltages in the valve rotor.

12. A method, comprising:
   providing a tool having an excitation coil, a sensing coil and at least one magnetic sensor;
   placing the positioning tool proximate an implantable medical device, the implantable medical device having a valve body and a valve rotor adjustable with respect to the valve body, the valve body including a resonant circuit and the valve rotor including a permanent magnet;
   energizing the resonant circuit using the excitation coil;
   sensing energy form the resonant circuit with the sensing coil;
   determining an orientation of the valve body with respect to the tool based on the sensed energy;
   determining a position of the valve rotor with respect to the positioning tool using the at least one magnetic sensor;
   determining a position of the valve rotor with respect to the valve body as a function of the orientation of the valve body and the position of the valve rotor with respect to the positioning tool.

13. The method of claim 12, further comprising:
   providing a stator with a plurality of stator coils in the tool;
   providing drive currents to the stator coils in the tool to adjust the position of the valve rotor with respect to the valve body.

14. The method of claim 12, further comprising:
   providing drive currents to the plurality of stator coils to induce electromagnetic force voltages in the permanent magnet of the valve rotor.

15. The method of claim 12 wherein the valve rotor is rotatable with respect to the valve body.

16. The method of claim 12, further comprising:
   determining a position of the valve rotor with respect to the tool using a plurality of magnetic sensors.

17. The method of claim 12, further comprising:
   calculating a valve setting for the implantable medical device from a plurality of valve settings, the valve setting being indicative of pressure and/or flow characteristics of fluid through the device.

18. The method of claim 12 wherein the plurality of stator coils include three stator coils that can be positioned equally about the valve rotor.

* * * * *